United States Patent [19]

Bischoff

[11] Patent Number: Plant 5,275

[45] Date of Patent: Aug. 28, 1984

[54] ROSE PLANT 'GINNY'

[75] Inventor: Francis Bischoff, Indianapolis, Ind.

[73] Assignee: John C. Walter, Grand Saline, Tex.

[21] Appl. No.: 417,412

[22] Filed: Sep. 13, 1982

[51] Int. Cl.[3] ..... A01H 5/00
[52] U.S. Cl. ..... Plt./7
[58] Field of Search ..... Plt./7

*Primary Examiner*—James R. Feyrer

*Attorney, Agent, or Firm*—Pearne, Gordon, Sessions, McCoy, Granger & Tilberry

[57] ABSTRACT

A new and distinct variety of miniature rose plant characterized by its buds and high-centered, heavy-petalled blooms of red and white borne in abundance throughout the growing season, and further characterized by the bushy upright plant, well-branched with fairly short internodes, which is easy to propagate from cuttings.

1 Drawing Figure

The present invention relates to a new and distinct variety named "Ginny" of rose plant of the miniature rose class, which was originated by my crossing as seed parent the floribunda rose known as "Little Darling," U.S. Plant Pat. No. 1,581, and the miniature rose known as "Toy Clown," U.S. Plant Pat. No. 2,909, as pollen parent.

Among the novel characteristics possessed by this new variety which distinguish it from its parents and all other varieties of which I am aware are: (1) high-centered blooms of red and white coloring, (2) an abundance of blooms with flowers borne singly, and occasionally several to a stem in a loose cluster, (3) each bloom heavily petalled (about 60 petals) to give a rounded effect when full-blown, (4) blooms of long-lasting quality, both on the plant and after cutting, (5) a well-proportioned plant which is vigorous, of rounded upright shape, and shows off its blooms well against its glossy, reddish-green and deep green foliage, and (6) branches with fairly short internodes.

The present variety of miniature rose was originated by me in Marion County, Ind. Carefully controlled conditions and asexual reproduction by cuttings of the new variety as performed by me in Marion County, Ind. show that the foregoing and other distinguishing characteristics come true to form and are established and transmitted through succeeding propagations.

The accompanying drawing shows a typical compact plant of the new variety with typical vegetative growth and buds and flowers in different stages of development, and as depicted in color as nearly true as it is reasonably possible to make the same in a color illustration of this character.

The following is a detailed description of my new rose variety, with color terminology in accordance with The Royal Horticultural Society Color Chart (RHSCC), except where common dictionary terms of color definition are employed.

Type: Hardy, dwarf, rounded bush, seedling, greenhouse, outdoors, cut flowers, garden decoration, potted plant.
Class: Miniature.

THE FLOWER

Observations were made from specimens grown outdoors at Marion County, Ind., U.S.A. in June 1982.

Type: Miniature.
Blooming habit: Recurrent.
Bud:
- *Size.*—Medium for miniature.
- *Form.*—Pear-shaped.
- *Color.*—When sepals first divide: white with red tip (52A and 52B). When petals begin to unfurl: white with red edges (52B). When half-blown: inside of petals — white and 20% edges shaded red (52C). Reverse side of petals — white with fine edge of red (52C).
- *Sepals.*—Half again as long as the bud-thin pointed 3 of the 5 are foliaceous.
- *Peduncle.*—*Average length* 1½", hairy, erect and stable, red changing to green in color.

Bloom:
- *Size.*—1¼ To 1½ inches when fully expanded.
- *Borne.*—Singly, occasional sprays.
- *Form.*—High-centered at first, opening to a slightly rounded bloom.
- *Petalage.*—About 60.
- *Color.*—During first two days: Inner petals at center of flower not visible until about 5th day. Outer petals — white with red border (52A and 52B). Base of petals (point of attachment) pale green. Reverse of petals — white-fine red edging (52A and 52B). General tonality from a distance — red buds (52A and 52B).
- *Color change.*—As bloom ages, red edges turn to pink (52D). General tonality — white blossoms with red edges (52A and 52B). After three or more days — white with pinkish red (52C and 52D).

Petals:
- *Texture.*—Thick.
- *Appearance.*—Inside, slightly velvety; Outside, dull satiny.
- *Form.*—Oval-small point at apex.
- *Arrangement.*—Regularly arranged.
- *Petaloids in center.*—Very few.
- *Persistence.*—Whole bloom and peduncle fall off when spent.
- *Fragrance.*—None.
- *Lasting quality.*—Extremely slow opening on plant, keeps long in refrigerator, good as cut flower.

REPRODUCTIVE ORGANS

Stamens, filaments, and anthers:

*Arrangement.*—Regular.
*Color.*—Yellow.
Pollen: Yellow.
Styles: Bunch, uneven length.
Stigmas:
*Color.*—Red.
Hips:
*Shape.*—Round.
*Size.*—$\frac{3}{8}''$ Diameter.
*Color.*—Orange-yellow when mature. One or two seeds protrude occasionally.

PLANT

Form: Upright and compact.
Growth: Vigorous and uniform branching.
*Height attained.*—15 To 18 inches.
Foliage: Mostly 5.
*Size.*—Medium for miniature.
*Quantity.*—Abundant.
*Color.*—New foliage: Upper side: Red. Underside: Red with pale green center. Old foliage: Upper side: Glossy dark green. Underside: Flat finish green.
*Shape.*—Ovate-pointed.
*Texture.*—Upper side: Smooth and glossy. Underside: Raised veins.
*Edge.*—Serrated.
*Serration.*—Uniform-fine indentations — denticulate.

*Leaf Stem.*—Color: Light green. Underside: Green.
*Stipules.*—Short — slightly bearded — pointed.
*Disease resistance.*—Blackspot — good. Mildew — fair. Rust — good.
Wood:
*New wood.*—Color: Red. Bark: Smooth.
*Old wood.*—Color: Green. Bark: Smooth.
Thorns:
*Thorns.*—Quantity: Very few on main stalks from base. Very few on laterals from stalk. Form: Straight and pointed. Length: $\frac{1}{8}''$. Color: Red when young. Position: Irregular.
*Prickles.*—Quantity: More prickles than thorns on main stalks. More prickles than thorns on laterals.
Winter hardiness: Needs some protection at 10° and lower. Mound of dirt or leaves.

I claim:

1. A new and distinct variety of rose plant of the miniature rose class, substantially as herein shown and described, characterized particularly by buds and flowers, which are generally white, edged with red in color, with many firm, thick petals, borne freely on a compact, bushy plant with reddish-green new foliage and dark green old foliage on branches with fairly short internodes, said plant being easy to propagate from cuttings, and said blooms being long-lasting both on the plant and as cut flowers.

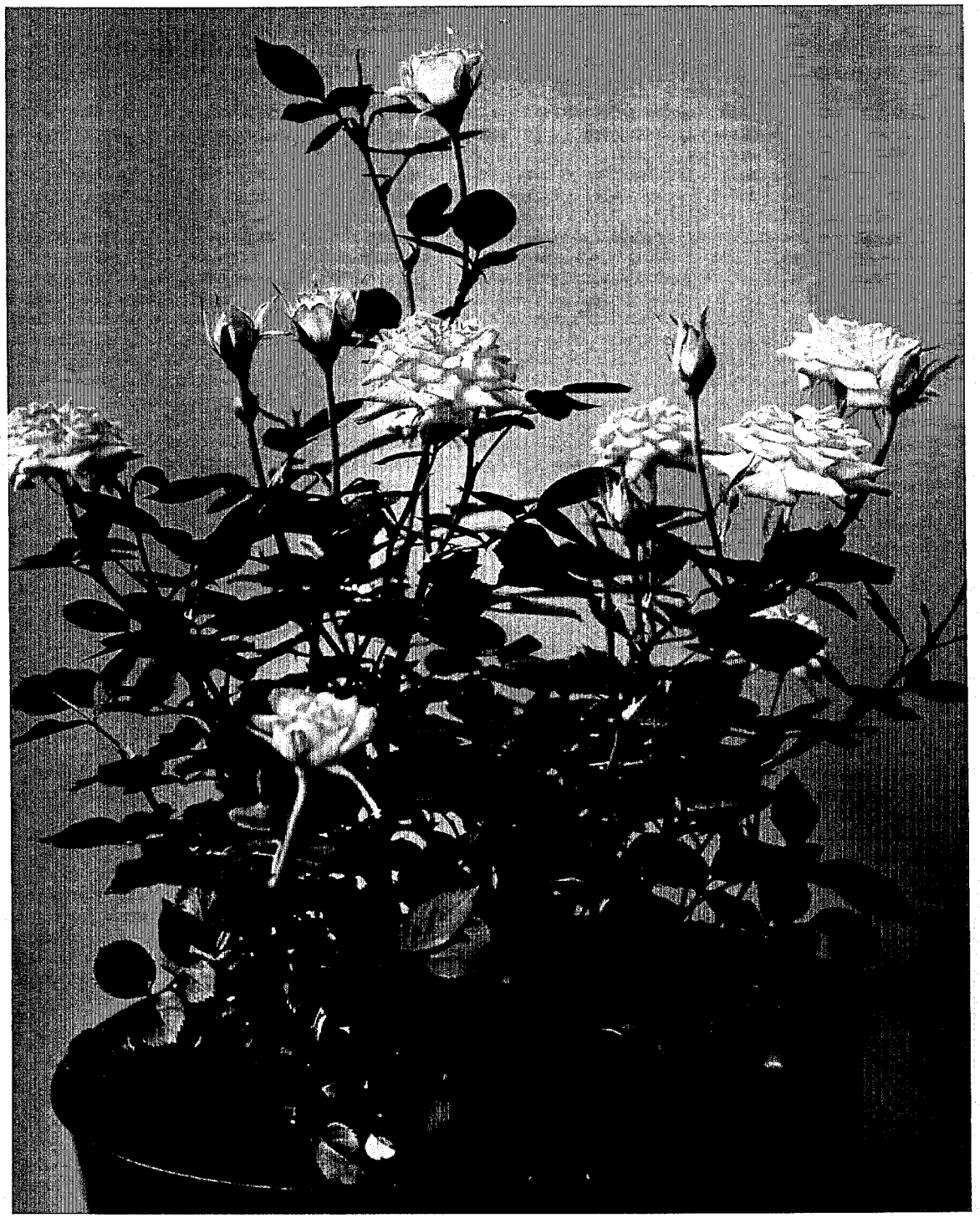

* * * * *